US00PP23845P2

(12) United States Plant Patent
Kordes

(10) Patent No.: US PP23,845 P2
(45) Date of Patent: Aug. 27, 2013

(54) MINIATURE ROSE PLANT NAMED 'KORBAILAND'

(50) Latin Name: *Rosa hybrida*
Varietal Denomination: KORbailand

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 255 days.

(21) Appl. No.: 13/065,651

(22) Filed: Mar. 25, 2011

(51) Int. Cl.
*A01H 5/00* (2006.01)

(52) U.S. Cl.
USPC ..... Plt./120

(58) Field of Classification Search
USPC ..... Plt./120
See application file for complete search history.

*Primary Examiner* — June Hwu
*Assistant Examiner* — Louanne Krawczewicz Myers

(57) ABSTRACT

A new and distinct variety of rose with long lasting, novel apricot and salmon flowers, and attractive foliage with good disease resistance. It exhibits uniform upright growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORbailand'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2004. The crossing was between an 'un-named seedling' and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORbailand'.

SUMMARY OF THE INVENTION

The new rose plant may be distinguished from its seed parent, an 'un-named seedling', by the following combination of characteristics:

1. The flower size of 'KORbailand' is medium while the flower size of the seed parent is small.
2. The shelf life of 'KORbailand' is significantly better than the shelf life of the seed parent.

The new rose plant may be distinguished from its pollen parent, an 'un-named seedling' by the following combination of characteristics:

1. The flower color of 'KORbailand' is apricot while the flower color of the pollen parent is copper yellow.
2. The bud shape of 'KORbailand' is rounded whereas the bud shape of the pollen parent is pointed.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORbailand' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORbailand' was selected in May 2005 from the seedling beds to be asexually propagated for further evaluation. The first asexual propagation of 'KORbailand' was done by budding to seedling understocks in August 2005 at the inventor's nursery in Offenseth-Sparrieshoop, Germany.

This initial and other subsequent propagations conducted in controlled environments demonstrate that 'KORbailand' reproduces true to type in successive generations of asexual reproduction.

BRIEF DESCRIPTION OF THE DRAWING

The accompanying drawing shows as true as is reasonably possible to obtain in color photographs of this type, the typical characteristics of the buds, flowers, reproductive organs, leaves, and stems of 'KORbailand'.

DETAILED BOTANICAL DESCRIPTION

The following is a description of 'KORbailand', as observed growing in February 2011 in a glasshouse in Surrey, British Columbia, Canada on plants of four months of age. Color references are made using The Royal Horticultural Society (London, England) Colour Chart, 2001 except where common terms of color are used.

For a comparison, several physical characteristics of the rose variety 'KORoskin', a rose variety from the same inventor described and illustrated in U.S. Plant Pat. No. 17,521 and issued on Mar. 27, 2007 are compared to 'KORbailand' in Chart 1.

CHART 1

| Characteristic | 'KORbailand' | 'KORoskin' |
|---|---|---|
| Flower color | Salmon apricot blend | Bronze yellow blend |
| Peduncle Length | 25-30 mm | 30-40 mm |
| Petal Reflex | Moderately reflexed | Slightly reflexed |

Parents:

*Seed parent*.—An 'un-named seedling'.

*Pollen parent*.—An 'un-named seedling'.

Classification:

*Botanical classification*.—*Rosa hybrida*, 'KORbailand'.

*Commercial classification*.—Miniature rose.

FLOWER AND FLOWER BUD

*Blooming habit*.—Recurrent.

*Flower bud*.—Size: Upon opening, 20 mm in length from base of receptacle to end of bud and 10 mm in diameter. Bud form: Long. High Centered. Bud color: As sepals first unfold, bud color is Red Group 38A. When ¼ open, the upper surface of petals is Orange-Red Group 32C, and the lower surface is Orange-Red Group 33C. The guard petals are Green Group 143C. Sepals: Color: Upper surface: Green Group 138B. Lower surface: Green Group 137C. Size: Average 25 mm long×5 mm wide. Base is flat at the union with peduncle. Shape: Sepals generally subulate. Sepal apex is pointed. Strong foliaceous appendages on three of the five sepals. Base is flat at union with receptacle. Quantity: Five. Margins: Entire, with foliaceous appendages on three of the sepals. Surface texture: Inner side: Pubescent. Outer surface: Light pubescence.

*Receptacle*.—Surface: Smooth. Color: Yellow-Green Group 144B. Shape: Funnel. Size: 10 mm (h)×8 mm (w).

*Peduncle*.—Surface: With moderate numbers of fine hairs and a limited number of stipitate glands. Length: 25 to 30 mm average length. Diameter: 2 to 4 mm average diameter. Color: Yellow-Green Group 144A. Strength: Strong. Borne: Singly, with each stem terminating in a peduncle bearing one flower. The inflorescence is simple, with a single flower born by a solitary stem.

Flower bloom:

*Fragrance*.—None.

*Duration*.—Long lasting. On the plant 12-16 days. As a cut flower, 6-8 days. Senesced petals drop away cleanly.

*Size*.—Medium sized blooms for a miniature rose. When open, the average flower diameter is 50 mm and the average flower depth is 15 mm.

*Form*.—Shape of flower when viewed from the side: Upon opening, upper part: Convex. Upon opening, lower part: Convex. Open flower, upper part: Flattened convex. Open flower, lower part: Flat.

Color:

*Upon opening, petals*.—Outermost petals: Outer Side: Red Group 38A. Inner Side: Red Group 49A. Innermost petals: Outer Side: Orange-Red Group 31C. Inner Side: Orange-Red Group 31C.

*Upon opening, basal petal spots*.—Basal petal spot, outermost petals: Outer Side: Green-Yellow Group 1C. Inner Side: Green-Yellow Group 1B. Basal petal spot, innermost petals: Outer Side: Green-Yellow Group 1B. Inner Side: Green-Yellow Group 1C.

*After opening, petals*.—Outermost petals: Outer Side: Red Group 47D. Inner Side: Red Group 43D. Innermost petals: Outer Side: Orange-Red Group 30D. Inner Side: Orange-Red Group 30C.

*After opening, basal petal spots*.—Basal petal spot, outermost petals: Outer Side: Green-Yellow Group 1C. Inner Side: Yellow Group 5A. Basal petal spot, innermost petals: Outer Side: Yellow Group 12A. Inner Side: Green-Yellow Group 1A. Variegations: None.

General tonality: On open flower Red Group 40D. No change in the general tonality at the end of the $8^{th}$ day.

Petals:

*Petal count*.—Average 25-35 petals under normal conditions. On average, 35 petaloids.

*Petal reflex*.—Moderate.

*Petal edge*.—With point in center of margin.

*Petal shape*.—Round.

*Apex shape*.—Mucronate.

*Base shape*.—Deltoid.

*Petal size*.—26 mm long×20 mm wide.

*Thickness*.—Average.

*Petal arrangement*.—Not formal.

Petaloids: Present.

*Petaloid size*.—Petaloids are 10 mm long and 8 mm wide.

*Petaloid color*.—Color of inner side is Orange-Red Group 32B. Color of outer side is Orange-Red Group 32B. Basal zone transitions to Yellow Group 13C.

*Petaloid texture*.—Smooth. Margins: Irregular, Undulated.

*Petaloid shape*.—Oblong. Apex: Round. Base: Deltoid.

Reproductive organs:

*Pistils*.—Abundant Approximately 20 present. Stigmas: Location: Inferior. Color: Yellow Group 9D. Styles: Length: 2 mm long. Color: Yellow Group 2C. Intonations of Red-Purple Group 58A.

*Stamens*.—Approximately 20 on average and regularly arranged. Anthers: Size: 1 mm long. Color: Yellow Group 8D. Pollen: Generally present. Color: Yellow Group 8D. Filaments: Color: Yellow Group 13A. Length: 3 mm.

THE PLANT

*Plant growth*.—Moderately vigorous. Compact and orderly growth. When grown as a 10.5 cm pot plant, the average height of the plant itself is 20-25 cm and the average plant width is 12-14 cm. Floriferous.

*Stems*.—Stem color: Young wood: Green Group 137D. Older wood: Green Group 137C. Stem surface: Young wood: Smooth. Older wood: Smooth.

*Prickles*.—Present. Incidence: 1-2 per 10 cm of stem. Size: Average length: 2 mm. Color: Immature prickles: none observed. Mature prickles: Yellow-Green Group 145B. Senescing to Greyed-Red Group 181D. Shape: Linear. Anthocyanin: None observed.

*Leaves and leaflets*.—Normally 5 leaflets on normal leaves in middle of the stem. Venation pattern: Pyramidal net pattern. Leaf size: 75 mm (l)×60 mm (w). Abundance/Quantity: Average. Texture: Upper side of leaflet: Semi glossy and smooth. Under side of leaflet: Matte and smooth. Color, mature foliage: Upper Leaf Surface: Green Group 137A. Lower Leaf Surface: Green Group 138B with intonations of Greyed-Purple Group 185C. Color, juvenile foliage: Upper Leaf Surface: Green Group 137B. Lower Leaf Surface: Green Group 138B. Anthocyanin intonation: Present Greyed Red Group 182B.

*Stipules*.—Size: Entire stipule is 8 mm long. Main body of stipule 4 mm in width. Stipule shape: Overall: Oblong Apices: Acuminate. Base: Truncate. Stipule color: Yellow-Green Group 144B. Anthocyanin Lacking. Presence of stipitate glands: Present on margins. Margins: With stipitate glands.

*Petiole*.—Length: 18 mm. Diameter: 2 mm. Petiole color: Green Group 137C with intonations of Green Group 137C present on juvenile foliage and stems. Underneath: Green Group 137D with moderate numbers of stipitate glands and prickles. Stipitate glands: Limited numbers of stipitate glands on margins.

*Petiole rachis*.—Length: 20 mm. Diameter: 1 mm. Color: Green Group 143C. Juvenile tissue lacking anthocyanin. Margins: Ridged. Prickles: A few small prickles underneath. Stipitate glands: Limited numbers of stipitate glands on margins.

*Leaflets*.—Size: Average size of the terminal leaflet is 40 mm (l)×24 mm (w). Shape: Elliptic. Base: Ovate. Apex: Acute. Margins: Denticulate. Texture: Upper surface: Smooth and Coriaccous. Lower, surface: Glabrous. Midrib lightly pubescent. Arrangement Oddly pinnate. Venation Reticulate.

Hips/seed formation: None observed.

Winter hardiness: To date, the variety has been grown successfully in Zone 7.

Disease resistance: Above average resistance to Powdery mildew (*Sphaerotheca pannosa*) and blackspot (*Diplocarpon rosae* diseases under normal glasshouse growing conditions.

I claim:

1. A new and distinct variety of rose plant, as described and illustrated herein.

* * * * *

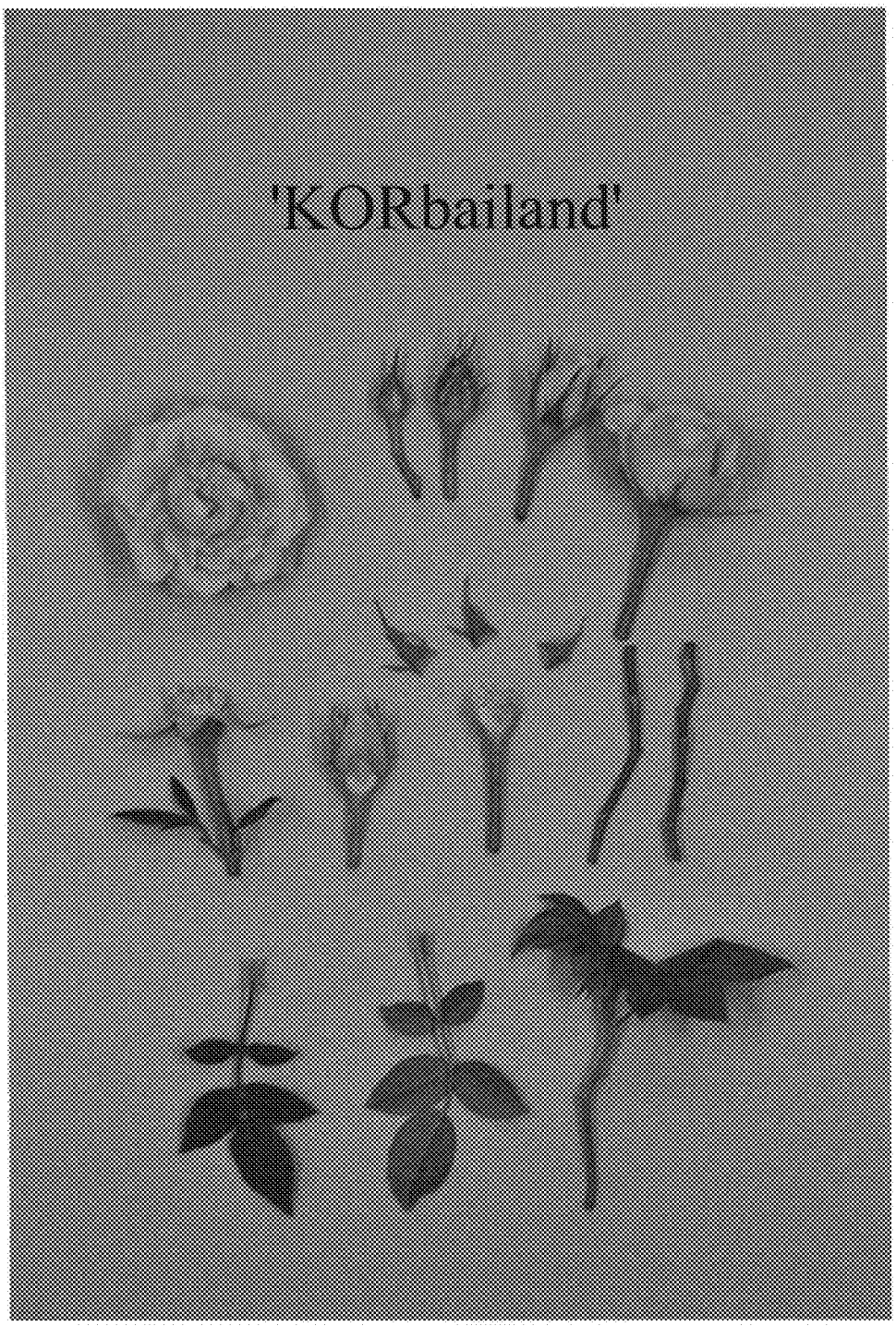
'KORbailand'